US010510440B1

(12) United States Patent
Jose

(10) Patent No.: US 10,510,440 B1
(45) Date of Patent: Dec. 17, 2019

(54) METHOD AND APPARATUS FOR IDENTIFYING MATCHING RECORD CANDIDATES

(71) Applicant: Change Healthcare Holdings, LLC, Nashville, TN (US)

(72) Inventor: Boban Jose, San Ramon, CA (US)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 697 days.

(21) Appl. No.: 14/450,910

(22) Filed: Aug. 4, 2014

Related U.S. Application Data

(63) Continuation of application No. 13/967,715, filed on Aug. 15, 2013, now abandoned.

(51) Int. Cl.
*G16H 10/60* (2018.01)

(52) U.S. Cl.
CPC .................. *G16H 10/60* (2018.01)

(58) Field of Classification Search
None
See application file for complete search history.

(56) References Cited

U.S. PATENT DOCUMENTS

| | | | |
|---|---|---|---|
| 5,664,109 A * | 9/1997 | Johnson ............... | G06F 19/322 705/2 |
| 5,991,758 A | 11/1999 | Ellard | |
| 5,999,937 A | 12/1999 | Ellard | |
| 6,397,224 B1 | 5/2002 | Zubeldia et al. | |
| 6,496,838 B1 | 12/2002 | Zamora-McKelvy et al. | |
| 6,523,019 B1 | 2/2003 | Borthwick | |
| 6,912,549 B2 | 6/2005 | Rotter et al. | |
| 6,922,695 B2 | 7/2005 | Skufca et al. | |
| 6,978,268 B2 | 12/2005 | Thomas et al. | |
| 6,988,075 B1 | 1/2006 | Hacker | |
| 6,996,565 B2 | 2/2006 | Skufca et al. | |

(Continued)

FOREIGN PATENT DOCUMENTS

| | | |
|---|---|---|
| CN | 102314478 A | 1/2012 |
| CN | 103310398 A | 9/2013 |

OTHER PUBLICATIONS

Wang, Xiaoyi 1962-, "Matching records in multiple databases using a hybridization of several technologies." (2008). Electronic Theses and Dissertations. Paper 1511. https://doi.org/10.18297/etd/1511 (Year: 2008).*

*Primary Examiner* — Devin C Hein
(74) *Attorney, Agent, or Firm* — Alston & Bird LLP

(57) ABSTRACT

A method, computing device and computer program product are provided to identify records that are associated with same person, even in instances in which the records are created and stored by different entities. In a method, a plurality of records are received, each having attributes associated with a person. For each record, the method determines a digest by determining a fuzzy representation of one or more of the attributes for the person and then combining representations of the attributes. The method also receives a query relating to a record for the person and determines a digest based upon the attributes of the person. In response to the query, the method identifies one or more records that are associated with respective individuals who are candidates to match the person based upon a comparison of representations of the digests of the records and the person.

18 Claims, 4 Drawing Sheets

(56) References Cited

U.S. PATENT DOCUMENTS

| | | |
|---|---|---|
| 7,167,858 B2 | 1/2007 | Naeymi-Rad et al. |
| 7,318,059 B2 | 1/2008 | Thomas et al. |
| 7,376,677 B2 | 5/2008 | Ober et al. |
| 7,440,094 B2 | 10/2008 | Yoo |
| 7,509,264 B2 | 3/2009 | Hasan et al. |
| 7,523,505 B2 | 4/2009 | Menschik et al. |
| 7,526,486 B2 | 4/2009 | Cushman, II et al. |
| 7,620,647 B2 | 11/2009 | Stephens et al. |
| 7,627,550 B1 | 12/2009 | Adams et al. |
| 7,685,093 B1 | 3/2010 | Adams et al. |
| 7,698,154 B2 | 4/2010 | Marchosky |
| 7,698,268 B1 | 4/2010 | Adams et al. |
| 7,707,047 B2 | 4/2010 | Hasan et al. |
| 7,725,331 B2 | 5/2010 | Schurenberg et al. |
| 7,801,878 B2 | 9/2010 | Hayes et al. |
| 7,856,366 B2 | 12/2010 | Dettinger et al. |
| 7,941,328 B2 | 5/2011 | Castille |
| 8,090,590 B2 | 1/2012 | Fotsch et al. |
| 8,095,386 B2 | 1/2012 | Lassetter et al. |
| 8,108,311 B2 | 1/2012 | Herlitz |
| 8,126,740 B2 | 2/2012 | Busch |
| 8,135,679 B2 | 3/2012 | Bayliss |
| 8,165,899 B2 | 4/2012 | Yeh et al. |
| 8,200,509 B2 | 6/2012 | Kenedy et al. |
| 8,249,895 B2 | 8/2012 | Faulkner et al. |
| 8,321,383 B2 | 11/2012 | Schumacher et al. |
| 8,321,393 B2 | 11/2012 | Adams et al. |
| 8,332,366 B2 | 12/2012 | Schumacher et al. |
| 8,356,009 B2 | 1/2013 | Ellard et al. |
| 8,359,339 B2 | 1/2013 | Adams et al. |
| 8,370,355 B2 | 2/2013 | Harger et al. |
| 8,370,366 B2 | 2/2013 | Adams et al. |
| 8,417,702 B2 | 4/2013 | Harger et al. |
| 8,423,382 B2 | 4/2013 | Dettinger et al. |
| 8,423,385 B2 | 4/2013 | Radoccia et al. |
| 8,423,514 B2 | 4/2013 | Goldenberg et al. |
| 8,429,220 B2 | 4/2013 | Wilkinson et al. |
| 8,438,182 B2 | 5/2013 | Gillam et al. |
| 8,452,619 B2 | 5/2013 | Kenedy et al. |
| 8,510,129 B2 | 8/2013 | Morris |
| 8,527,295 B2 | 9/2013 | D'Ambrosia |
| 8,620,930 B2 | 12/2013 | Gulhane et al. |
| 8,621,244 B1 | 12/2013 | Rembert et al. |
| 2004/0102998 A1 | 5/2004 | Bao et al. |
| 2005/0222876 A1 | 10/2005 | Iwayama et al. |
| 2006/0080312 A1 | 4/2006 | Friedlander et al. |
| 2008/0091474 A1* | 4/2008 | Ober ............... G06F 19/324 705/3 |
| 2008/0126133 A1* | 5/2008 | Park ............... G06Q 10/10 705/3 |
| 2009/0024417 A1 | 1/2009 | Marks et al. |
| 2009/0089317 A1 | 4/2009 | Ford et al. |
| 2009/0150451 A1 | 6/2009 | Gejdos et al. |
| 2009/0198686 A1 | 8/2009 | Cushman, II et al. |
| 2009/0326982 A1 | 12/2009 | Deobhakta et al. |
| 2010/0114877 A1 | 5/2010 | Adams et al. |
| 2010/0131298 A1 | 5/2010 | Buttner et al. |
| 2010/0179834 A1 | 7/2010 | Wager |
| 2011/0010401 A1 | 1/2011 | Adams et al. |
| 2011/0106564 A1 | 5/2011 | Hachmeister et al. |
| 2011/0191349 A1 | 8/2011 | Ford et al. |
| 2011/0246230 A1 | 10/2011 | Sie et al. |
| 2011/0246234 A1 | 10/2011 | Irwin et al. |
| 2011/0246237 A1 | 10/2011 | Vdovjak |
| 2011/0246238 A1 | 10/2011 | Vdovjak |
| 2011/0282688 A1 | 11/2011 | Raggousis |
| 2012/0010904 A1 | 1/2012 | Buck et al. |
| 2012/0059668 A1 | 3/2012 | Baldock et al. |
| 2012/0072237 A1 | 3/2012 | Campbell et al. |
| 2012/0078663 A1 | 3/2012 | Lorsch |
| 2012/0089604 A1* | 4/2012 | Hamilton ......... G06F 17/30303 707/737 |
| 2012/0095923 A1 | 4/2012 | Herlitz |
| 2012/0109685 A1 | 5/2012 | Carter et al. |
| 2012/0150887 A1 | 6/2012 | Clark et al. |
| 2012/0203576 A1 | 8/2012 | Bucur et al. |
| 2012/0245954 A1 | 9/2012 | Klotz et al. |
| 2012/0246741 A1 | 9/2012 | Klotz et al. |
| 2012/0284056 A1 | 11/2012 | Hofstetter |
| 2013/0066901 A1* | 3/2013 | Marcelais ......... G06F 17/30097 707/769 |
| 2013/0080192 A1 | 3/2013 | Bucur et al. |
| 2013/0179186 A1 | 7/2013 | Birtwhistle et al. |
| 2013/0204880 A1 | 8/2013 | Lesiecki et al. |
| 2013/0262141 A1 | 10/2013 | Crockett |
| 2013/0290032 A1 | 10/2013 | Netsch et al. |

* cited by examiner

METHOD AND APPARATUS FOR IDENTIFYING MATCHING RECORD CANDIDATES

CROSS REFERENCE TO RELATED APPLICATION

This application is a continuation of and claims priority to U.S. application Ser. No. 13/967,715, filed on Aug. 15, 2013, the entire contents of which are hereby incorporated by reference.

TECHNOLOGICAL FIELD

An example embodiment of the present invention relates generally to the identification of records and, more particularly, to the identification of records, such as for patients, who are candidates to match a person who is associated with another record.

BACKGROUND

A variety of different types of records may be stored in an electronic format so as to facilitate the identification, retrieval and sharing of the records while correspondingly reducing the need for physical records. One type of record that is being increasingly stored in an electronic format is a patient record. A patient record may be maintained by a healthcare facility and may include information regarding a patient, such as various demographic attributes of the patient, e.g., name, address, date of birth, etc., and encounters of the patient with the healthcare facility. A patient record may also include or be associated with other information, such as one or more documents related to the patient's healthcare including, for example, the physician's notes, lab results and/or images of the patient, e.g., x-rays, magnetic resonance imaging (MRI) images, computer aided tomography (CAT) scans, etc.

Some patients may visit multiple healthcare facilities over the course of time. These healthcare facilities may be owned and operated by different healthcare organizations. Each healthcare facility may maintain a patient record, but the patient records maintained by the different healthcare facilities may be independent of one another since the different healthcare organizations that own and operate the healthcare facilities may not share patient records or otherwise cooperate to maintain a common patient record.

In order to have a more complete and comprehensive understanding of a patient's health, a physician or other healthcare practitioner may wish to have access to all of the patient records, regardless of the healthcare facility that created and maintains the patient records. However, in an instance in which a patient has visited multiple healthcare facilities that are owned or operated by different healthcare organizations and unless the patient has collected and provides a physician or other healthcare practitioner with all of their patient records from the various healthcare facilities that they have visited, the physician or other healthcare practitioner may have difficulty accessing or be unable to access the plurality of patient records maintained for the patient by the various healthcare facilities. This difficulty may be exacerbated by the assignment of a different, unique patient identifier to the patient by at least some of the healthcare facilities since a healthcare practitioner may be unaware of the patient identifier associated with the patient by other healthcare facilities and, as such, may have difficulty identifying the patient to the other healthcare facilities.

As such, a healthcare practitioner may find it difficult to readily access all of the patient records created and stored by the various healthcare facilities that have treated the patient in the past. Thus, a healthcare practitioner may not have the benefit of the information contained in at least some of the patient records maintained by other healthcare facilities, thereby potentially reducing the efficiency with which the healthcare practitioner may treat a patient.

BRIEF SUMMARY

A method, computing device and computer program product are provided according to an example embodiment in order to identify records that are associated with same person, even in instances in which the records are created and stored by different entities. In this regard, the method, computing device and computer program product may permit a large number of records to be searched in an efficient manner in order to identify a subset of the records that may be associated with the same person. As such, the method, computing device and computer program product permit a more comprehensive review of the records associated with the person even in instances in which a voluminous number of records are to be considered.

In one embodiment, a method is provided that includes receiving a plurality of records with each record having plurality of attributes associated with a person. For each record, the method of this embodiment determines, with processing circuitry, a digest. The method may determine the digest by determining a fuzzy representation of one or more of the plurality of demographic attributes for the respective person and combining representations of one or more of the demographic attributes associated with the respective person including the fuzzy representation of one or more of the plurality of demographic attributes associated with the respective person. The method of this embodiment also receives a query relating to a patient record for the person and determines a digest based upon the demographic attributes associated with the person. In response to the query, the method of this embodiment identifies one or more records that are associated with respective individuals who are candidates to match the person based upon a comparison of representations of the digests of the records and a representation of the digest of the person.

The method may determine various types of fuzzy representations depending upon the type of demographic attribute. For example, the method may determine a fuzzy representation of a name by determining a phonetic representation of at least a subset of the name. As another example, the method may determine a fuzzy representation of a date by determining a representation of the date with less specificity than a respective day. In this embodiment, the method may determine a representation of the date based upon a week, a month, a year or decade of the respective date.

The method of one embodiment may determine a digest by determining, for at least some records, a plurality of digests. For example, the plurality of digests may be based upon a typographical error in a demographic attribute, a transposition of first and last names of an individual and/or a transposition of a day and a month of a date. A method of one embodiment may also include hashing the digests of the records and hashing the digest of the person such that the comparison is based upon hashed representations of the digests of the records and a hashed representation of the digest of the person.

The method of one embodiment may also include, for each record that was identified, determining a confidence score by comparing the plurality of demographic attributes associated with the respective individual to corresponding demographic attributes of the person. The method of this embodiment may also include identifying one or more records that are associated with respective individuals who match the person based upon the confidence scores.

In another embodiment, a computing device is provided that includes a processing circuitry that is configured to receive a plurality of records with each record having plurality of attributes associated with a person. For each record, the processing circuitry may be configured to determine a digest. The processing circuitry may determine the digest by determining a fuzzy representation of one or more of the plurality of demographic attributes for the respective person and combining representations of one or more of the demographic attributes associated with the respective person including the fuzzy representation of one or more of the plurality of demographic attributes associated with the respective person. The processing circuitry of this embodiment is also configured to receive a query relating to a patient record for the person and to determine a digest based upon the demographic attributes associated with the person. In response to the query, the processing circuitry of this embodiment is configured to identify one or more records that are associated with respective individuals who are candidates to match the person based upon a comparison of representations of the digests of the records and a representation of the digest of the person.

The processing circuitry may be configured to determine various types of fuzzy representations depending upon the type of demographic attribute. For example, the processing circuitry may be configured to determine a fuzzy representation of a name by determining a phonetic representation of at least a subset of the name. As another example, the processing circuitry may be configured to determine a fuzzy representation of a date by determining a representation of the date with less specificity than a respective day. In this embodiment, the processing circuitry may be configured to determine a representation of the date based upon a week, a month, a year or decade of the respective date.

The processing circuitry of one embodiment may be configured to determine a digest by determining, for at least some records, a plurality of digests. For example, the plurality of digests may be based upon a typographical error in a demographic attribute, a transposition of first and last names of an individual and/or a transposition of a day and a month of a date. The processing circuitry of one embodiment may also be configured to hash the digests of the records and to hash the digest of the person such that the comparison is based upon hashed representations of the digests of the records and a hashed representation of the digest of the person.

The processing circuitry of one embodiment may also be configured, for each record that was identified, to determine a confidence score by comparing the plurality of demographic attributes associated with the respective individual to corresponding demographic attributes of the person. The processing circuitry of this embodiment may also be configured to identify one or more records that are associated with respective individuals who match the person based upon the confidence scores.

In a further embodiment, a computer program product is provided that includes a non-transitory computer readable storage medium having program code portions stored thereon with the program code portions configured, upon execution, to receive a plurality of records. Each record has plurality of attributes associated with a person. For each record, the program code portions may be configured to determine a digest. The program code portions may be configured to determine the digest by determining a fuzzy representation of one or more of the plurality of demographic attributes for the respective person and combining representations of one or more of the demographic attributes associated with the respective person including the fuzzy representation of one or more of the plurality of demographic attributes associated with the respective person. The program code portions are also configured to receive a query relating to a patient record for the person and to determine a digest based upon the demographic attributes associated with the person. In response to the query, the program code portions of this embodiment are also configured to identify one or more records that are associated with respective individuals who are candidates to match the person based upon a comparison of representations of the digests of the records and a representation of the digest of the person.

The program code portions may be configured to determine various types of fuzzy representations depending upon the type of demographic attribute. For example, the program code portions may be configured to determine a fuzzy representation of a name by determining a phonetic representation of at least a subset of the name. As another example, the program code portions may be configured to determine a fuzzy representation of a date by determining a representation of the date with less specificity than a respective day. In this embodiment, the program code portions may be configured to determine a representation of the date based upon a week, a month, a year or decade of the respective date.

The program code portions of one embodiment may be configured to determine a digest by determining, for at least some records, a plurality of digests. For example, the plurality of digests may be based upon a typographical error in a demographic attribute, a transposition of first and last names of an individual and/or a transposition of a day and a month of a date. The program code portions of one embodiment may also be configured to hash the digests of the records and to hash the digest of the person such that the comparison is based upon hashed representations of the digests of the records and a hashed representation of the digest of the person.

The program code portions of one embodiment may also be configured, for each record that was identified, to determine a confidence score by comparing the plurality of demographic attributes associated with the respective individual to corresponding demographic attributes of the person. The program code portions of this embodiment may also be configured to identify one or more records that are associated with respective individuals who match the person based upon the confidence scores.

BRIEF DESCRIPTION OF THE DRAWINGS

Figure 1:
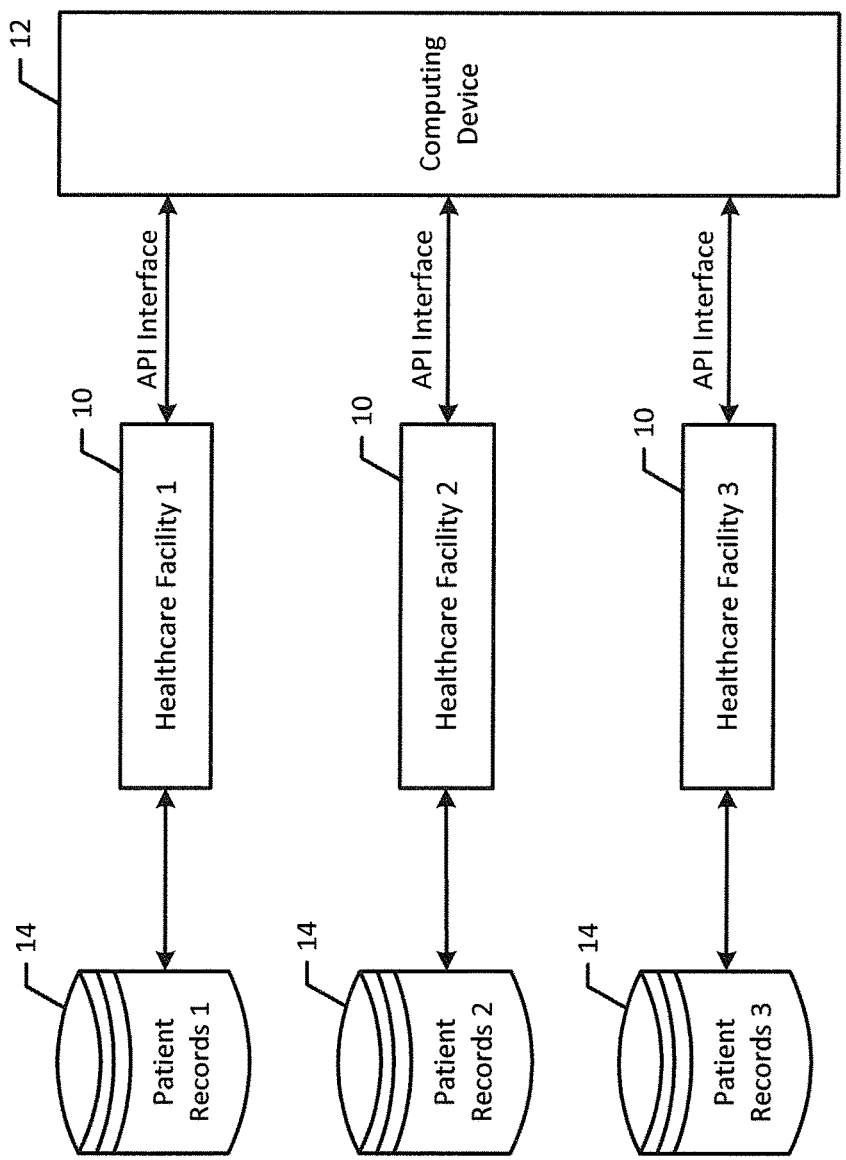
Figure 2:
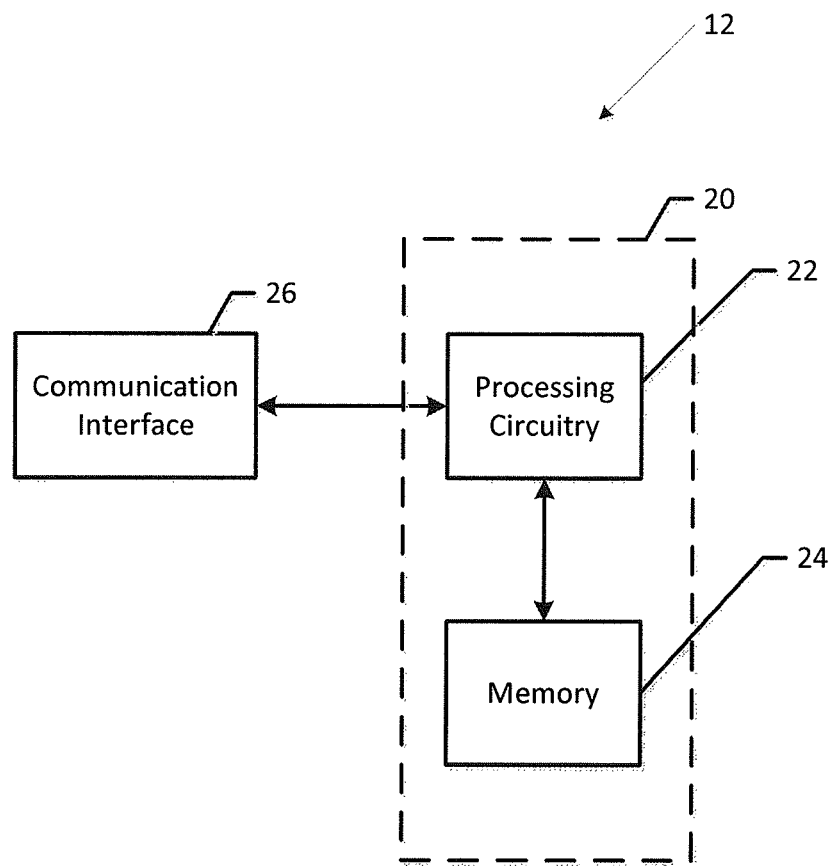
Figure 3:
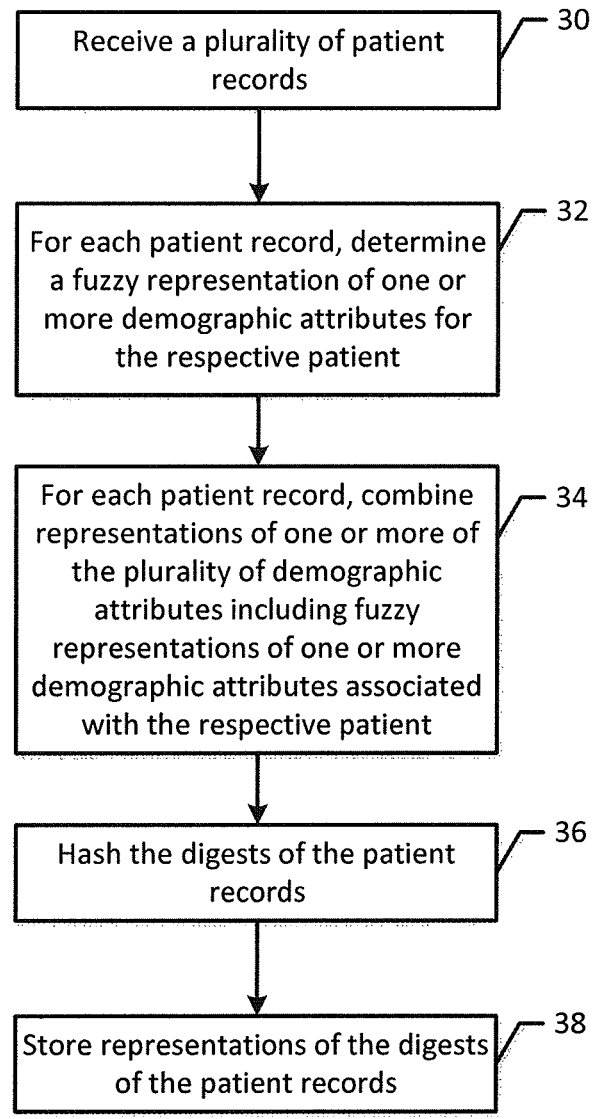
Figure 4:
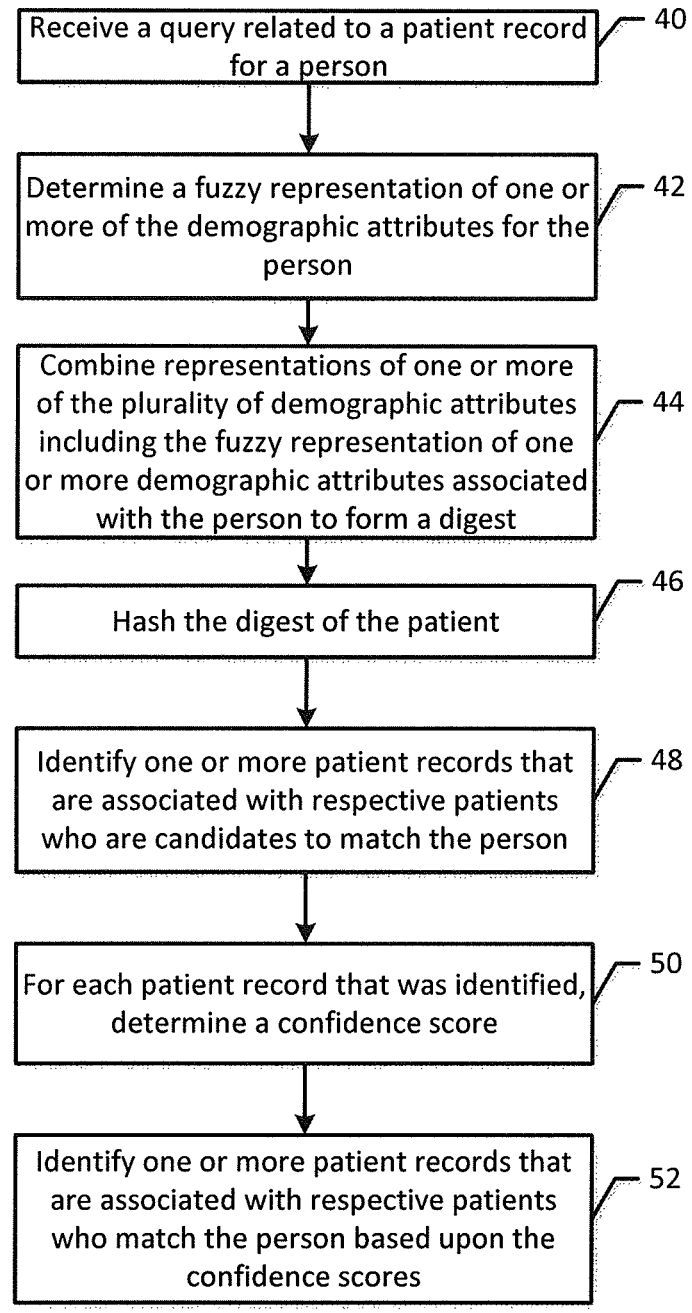

Having thus described certain example embodiments of the invention in general terms, reference will now be made to the accompanying drawings, which are not necessarily drawn to scale, and wherein:

FIG. 1 is a schematic representation of a system for processing patient records that may be specifically configured in accordance with an example embodiment of the present invention;

FIG. 2 is a block diagram of a computing device that may be specifically configured in accordance with an example embodiment of the present invention;

FIG. 3 is a flow chart illustrating operations performed, such as by the computing device of FIG. 2, in conjunction with receiving patient records and determining corresponding digests in accordance with an example embodiment of the present invention; and FIG. 4 is a flow chart illustrating operations performed, such as by the computing device of FIG. 2, in conjunction with identifying one or more patient records that are associated with respective patients who are candidates to match a particular person who is associated with another patient record in accordance with an example embodiment of the present invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Further, the apparatus and method of example embodiments of the present invention will be primarily described in conjunction with medical-imaging applications. It should be understood, however, that the apparatus and method may be utilized in conjunction with a variety of other applications, both in the medical industry and outside the medical industry. Like numbers refer to like elements throughout.

A method, computing device and computer program product are provided in accordance with an example embodiment in order to process records so as to identify one or more records that are associated with respective individuals who are candidates to match a person of interest. In this regard, the method, computing device and computer program product of the example embodiment may be configured to process a wide variety of different types of records such as tax records, employment records, criminal records, student records or any other type of structured data having demographic attributes associated with an individual.

By way of example, but not of limitation, the method, apparatus and computer program product will be hereinafter described in conjunction with the processing of patient records in order to identify one or more patient records that are associated with respective patients who are candidates to match a person of interest. Each patient record may include a plurality of demographic attributes associated with the patient, such as the first, middle and last name of the person, the mailing address of the person, the date of birth of the person, etc. Additionally, a patient record may include information describing one or more encounters of a patient with a respective healthcare facility. Patient records may include information regarding a wide variety of encounters including office visits, laboratory tests, hospital admittances, imaging appointments, etc. Some patient records may also include or otherwise be associated with one or more documents. The documents may be associated with one or more of the encounters for which the patient record includes information. The documents may include, for example, laboratory results, notes taken by a physician during an office visit, imaging studies or the like.

The patient records may be created by the healthcare facility that treats the patient. In instances in which the patient has visited a plurality of different healthcare facilities, the patient may have patient records that have been created by each of the plurality of different healthcare providers. Each healthcare facility may store the patient records for the patients that have been treated by the respective healthcare facility in order to memorialize the health care provided to the patient by the respective healthcare facility. As such, the patient records created by a plurality of healthcare facilities for respective patients are not generally stored in a common database, but are, instead, stored in a distributed fashion amongst the plurality of healthcare providers.

Although each healthcare facility may assign a patient identifier for each patient treated by the respective healthcare facility that is unique within the healthcare facility, a patient is not generally assigned a universal patient identifier that uniquely identifies the patient relative to each of the healthcare facilities. In order to facilitate the identification of patient records that are associated with respective patients who are candidates to match a person in question, information regarding the patient records, such as the information regarding the demographic attributes associated with the patient, may be provided by the healthcare facilities to a computing device that may be configured to identify patient records associated with respective patients who are candidates to match the person in question.

While such a system of healthcare facilities may be configured in various manners, FIG. 1 illustrates a block diagram of an example network infrastructure in accordance with example embodiments of the present invention. The example network infrastructure includes a plurality of healthcare facilities 10 in communication with a computing device 12, such as via respective application programming interfaces (APIs) or via a portal application, e.g., a web browser interface. Although three healthcare facilities are depicted in FIG. 1, the system may include any number of healthcare facilities. The healthcare facilities may include any of a variety of facilities visited by a patient that may create and maintain patient records including hospitals, physician practices, laboratories, imaging facilities or the like. As shown in FIG. 1, each healthcare facility may include or otherwise be in communication with a memory device for maintaining a database 14 of patient records for patients who have been treated at the respective healthcare facility. As described below, the computing device 12 may be configured to receive patient records from the healthcare facilities 10 and to identify patient records associated with respective patients (regardless of the healthcare facility that provided the patient records) who are candidates to match a person in question, such as a person seeking admittance by one of the healthcare facilities.

FIG. 2 illustrates a block diagram of a computing device 12 in accordance with some example embodiments. The computing device is capable of functioning in a health information infrastructure and may be embodied by one or more servers, computer workstations, desktop or laptop computers or the like. As described below, the computing device may be configured to implement and/or otherwise support implementation of various example embodiments. However, it should be noted that the components, devices or elements illustrated in and described with respect to FIG. 2 below may not be mandatory and thus some may be omitted in certain embodiments. Additionally, some embodiments may include further or different components, devices or elements beyond those illustrated in and described with respect to FIG. 2.

The computing device 12 may include or otherwise be in communication with processing circuitry 20 that is configurable to perform actions in accordance with one or more example embodiments disclosed herein. In this regard, the processing circuitry may be configured to perform and/or control performance of one or more functionalities of the computing device in accordance with various example embodiments, and thus may provide means for performing functionalities of the computing device. The processing circuitry may be configured to perform data processing, application execution and/or other processing and management services according to one or more example embodiments.

In some example embodiments, the processing circuitry 20 may include a processor 22 and, in some embodiments, such as that illustrated in FIG. 1, may further include memory 24. The processing circuitry may be in communication with or otherwise control a communication interface 26 and, in some embodiments, a user interface (not shown). As such, the processing circuitry may be embodied as a circuit chip (e.g., an integrated circuit chip) configured (e.g., with hardware, software or a combination of hardware and software) to perform operations described herein.

The processor 22 may be embodied in a number of different ways. For example, the processor may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of the computing device 12 as described herein. The plurality of processors may be embodied on a single computing device or distributed across a plurality of computing devices collectively configured to function as the apparatus 102. In some example embodiments, the processor may be configured to execute instructions stored in the memory 24 or otherwise accessible to the processor. As such, whether configured by hardware or by a combination of hardware and software, the processor may represent an entity (e.g., physically embodied in circuitry—in the form of processing circuitry 20) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform one or more operations described herein.

In some example embodiments, the memory 24 may include one or more non-transitory memory devices such as, for example, volatile and/or non-volatile memory that may be either fixed or removable. In this regard, the memory may comprise a non-transitory computer-readable storage medium. It will be appreciated that while the memory is illustrated as a single memory, the memory may comprise a plurality of memories. The plurality of memories may be embodied on a single computing device or may be distributed across a plurality of computing devices collectively configured to function as the computing device 12. The memory may be configured to store information, data, applications, instructions and/or the like for enabling the computing device to carry out various functions in accordance with one or more example embodiments. For example, the memory may be configured to buffer input data for processing by the processor 22. Additionally or alternatively, the memory may be configured to store instructions for execution by the processor. As yet another alternative, the memory may include one or more databases that may store a variety of files, contents or data sets. Among the contents of the memory, applications may be stored for execution by the processor in order to carry out the functionality associated with each respective application. In some cases, the memory may be in communication with one or more of the processor, user interface, or communication interface 26 via a bus or buses for passing information among components of the computing device.

The user interface may be in communication with the processing circuitry 20 to receive an indication of a user input at the user interface and/or to provide an audible, visual, mechanical or other output to the user. As such, the user interface may include, for example, a keyboard, a mouse, a joystick, a display, a touch screen display, a microphone, a speaker, a Light Emitting Diode (LED), a lighting device, an electronic sensor for capturing human body movements, and/or other input/output mechanisms. In embodiments in which the computing device 12 is implemented on a server, aspects of the user interface may be limited, or the user interface may even be eliminated. For example, the computing device may act as a server or host device, with a user interface provided by a client application.

The communication interface 26 may include one or more interface mechanisms for enabling communication with other devices and/or networks, such as with the healthcare facilities. In this regard, communication with the healthcare facilities includes communication with one or more computing devices of the respective healthcare facilities. In some cases, the communication interface may be any means such as a device or circuitry embodied in either hardware, or a combination of hardware and software that is configured to receive and/or transmit data from/to a network and/or any other device or module in communication with the processing circuitry 20. By way of example, the communication interface may be configured to enable the computing device 12 to communicate with the healthcare facilities 10 via a wireless network, such as a wireless local area network (WLAN), cellular network, and/or the like. Additionally or alternatively, the communication interface may be configured to enable the computing device to communicate with the healthcare facilities via a wireline network. In some example embodiments, the communication interface may be configured to enable communication between the computing device and one or more healthcare facilities via the internet. Accordingly, the communication interface may, for example, include an antenna (or multiple antennas) and supporting hardware and/or software for enabling communications with a wireless communication network (e.g., a wireless local area network, cellular network, and/or the like) and/or a communication modem or other hardware/software for supporting communication via cable, digital subscriber line (DSL), universal serial bus (USB), Ethernet or other methods.

Having now described computing device 12 configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

As shown in block 30 of FIG. 3, the computing device 12 may include means, such as the processing circuitry 20, the processor 22, the communication interface 26 or the like, for receiving a plurality of patient records. In one embodiment, the computing device may be configured to receive feeds of patient records from each of a plurality of healthcare facilities 10. Although the patient records may be received in batches or at pre-defined intervals, the computing device of one embodiment may be configured to receive the patient record upon the admittance of a patient by a healthcare facility. Although the computing device may receive the entire patient record including information regarding the various encounters and any documents included within or otherwise associated with the patient record, the computing device of one embodiment may be configured to receive only a portion of the patient record, such as the information defining the demographic attributes associated with the patient, and not the information associated with the encounters of the patient with the healthcare facility or the documents included within or otherwise associated with the patient record. Regardless, reference herein to patient records includes the entirety of a patient record as well as selected portions of a patient record, such as the information the defines the demographic attributes associated with the patient.

The computing device 12 may also include means, such as the processing circuitry 20, the processor 22 or the like, for determining, for each patient record that is received from a healthcare facility 10, a digest that includes representations of one or more of the plurality of the demographic attributes associated with the respective patient. In this regard, the computing device, such as the processing circuitry, may be configured to determine a fuzzy representation of one or more of the plurality of demographic attributes for the respective patient. See block 32 of FIG. 3. As used herein, a fuzzy representation of a demographic attribute is a representation of the demographic attribute with less specificity than is provided by the demographic attribute itself. As such, a fuzzy representation of a demographic attribute may be an approximation or estimation of the demographic attribute.

Various types of fuzzy representations of demographic attributes may be provided depending upon the type of demographic attribute. With respect to a name or other word or phrase, the computing device 12, such as the processing circuitry 20, may be configured to determine the fuzzy representation by determining a phonetic representation of at least a subset of the name or other word or phrase. The computing device, such as the processing circuitry, may be configured to implement various phonetic algorithms, such as the Soundex phonetic algorithm, to determine the phonetic representation of at least a subset of the name or other word or phrase. With respect to the name, for example, the computing device, such as the processing circuitry, may be configured to determine a phonetic representation of the first name and/or a phonetic representation of the last name. In an example of a person named Stephan Gauss, the computing device, such as the processing circuitry, may employ the Soundex phonetic algorithm to represent the first name Stephan as S315 and the last name Gauss as G200.

With respect to a date or other numerical value, the computing device 12, such as the processing circuitry 20, may be configured to determine the fuzzy representation by determining a representation of the date or the numerical value with less specificity than the respective day or the numerical value. In this regard, the computing device, such as the processing circuitry, may determine the representation of the date by determining the representation of the date based upon the week, month, year or a decade of a respective day, that is, the week, month, year or decade within which the respective day lies. For example, the day may be Jan. 15, 2013. As such, the computing device, such as the processing circuitry, may determine the representation of the date based upon the week by representing the day as 3 for the third week of the year, based upon the month by representing the day as 1 for the month of January, based upon the year as 2013 for the year in which the day falls or based upon the decade as 2010 for the decade in which the day falls. As another example of a fuzzy representation of a numerical value, the computing device, such as the processing circuitry, may be configured to represent the zip code based upon the leftmost one, two or three numbers of the zip code without inclusion of the remaining digits of the zip code so as to effectively define a broader region within which the respective zip code falls.

In conjunction with the determination of the digest and as shown in block 34 of FIG. 3, the computing device 12 may include means, such as the processing circuitry 20, the processor 22 or the like, for combining representations of one or more of the plurality of demographic attributes associated with respective patients including the fuzzy representation of one or more of the plurality of demographic attributes associated with respective patient. Thus, representations of one or more demographic attributes are combined by the processing circuitry with at least one of the representations being a fuzzy representation of a demographic attribute. In this regard, each of the representations of the one or more demographic attributes that are combined to form the digest may be fuzzy representations of a respective demographic attributes. For example, a digest for a person named Stephan Gauss who was born on Oct. 10, 1967 may be created entirely of fuzzy representations of the demographic attributes by including the soundex representations of Stephan (S315) and Gauss (G200) and the decade (1970) in which he was born, such as S315G2001970. Alternatively, the representations of the one or more demographic attributes that are combined to form the digest may include one or more fuzzy representations of respective demographic attributes and one or more representations of the demographic attributes that have not been approximated or otherwise subjected to a fuzzy representation. For example, a computing device, such as the processing circuitry, may be configured to combine fuzzy representations of the first and last names of a patient along with exact date of birth of the patient. With respect to the foregoing example involving Stephan Gauss, this resulting digest may be S315G20010101976.

As described, the computing device 12, such as the processing circuitry 20, may be configured to determine a digest for the demographic attributes associated with each patient record that is received. The digest that is determined may be stored, such as in memory 24, in association with the patient record. For example, both the patient record that is received from the healthcare facility 10 and the resulting digest may be stored in memory and, in one embodiment, the digest may be associated with the patient records, such as by being linked to the respective patient records. Thus, the computing device may include means, such as the processing circuitry, the memory or the like, for storing representations of the digests of the patient records as shown in block 38 of FIG. 3.

In one embodiment, the computing device 12 may include means, such as the processing circuitry 20, the processor 22 or like, for determining a plurality of digests for at least some patient records. As such, for a single patient record, the computing device, such as the processing circuitry, may define a plurality of digests. These digests may include representations of different combinations of the demographic attributes. For example, a first digest may include a representation of a first name, but no representation of the last name so as to facilitate the subsequent identification of patient records (as described below) for which the last name of the patient has changed. Additionally, a second digest may include a representation of the last name of the patient, but not the first name of the patient so as to facilitate identification of other patient records for the same patient that may have included a different first name, such as a nickname, a first initial or a shortened version of the first name.

As another example, the computing device 10, such as the processing circuitry 12, may define one or more digests based upon anticipated typographical errors in at least one of the demographic attributes. In this regard, the computing device, such as the processing circuitry, may be informed of or otherwise be configured to identify the most common typographical errors, such as by spelling Stephan as Stephen in the foregoing example of Stephan Gauss, and may be configured to determine digests based upon combinations of representations of the same demographic attributes with one or more of the demographic attributes used in the creation of one or more of the digests having a typographical error. For example, a first digest may be created based upon representations of the first name Stephan, the last name Gauss and the date of birth of Oct. 10, 1967, a second digest may be created based upon representations of the first name Stephen (including a typographical error), the last name Gauss and the date of birth of Oct. 10, 1967 and a third digest may be created based upon representations of the first name Stephn (including a typographical error), the last name Ghosh (including a typographical error) and the date of birth of Oct. 10, 1965 (including a typographical error). As another example, the computing device 12, such as the processing circuitry 20, may be configured to determine a digest based upon a transposition of the first and last names of a respective patient or a transposition of the day and month of the date since such transpositions are not uncommon in conjunction with the demographic attributes included within a patient record. By determining a plurality of digests, the computing device facilitates the identification of patient records that may include the same typographical errors, transpositions or the like.

In one embodiment, the computing device 12 may include means, such as the processing circuitry 20, the processor 22 or the like, for hashing the digest(s) for the patient record prior to storing the digest(s). See block 36 of FIG. 3. In one embodiment, the computing device, such as the processing circuitry, may then be configured to store the hashed representation of the digest of the patient record, such as in memory 24. See block 38 of FIG. 3. As such, the computing device may maintain one or more digests associated with each of the patient records that have been received from the plurality of healthcare facilities 10.

Referring now to FIG. 4, the computing device 12 may not only create digests of the patient records received from the healthcare facilities 10, but may also identify those patient records for which digests have been created that are associated with patients who are candidates to match a particular person, such as a person seeking admittance at a respective health care facility. As such, the computing device may also include means, such as the processing circuitry 20, the processor 22, the communications interface 26 or the like, for receiving a query related to a patient record for a person. See block 40 of FIG. 4. The query may be received from a healthcare facility at which the person has arrived and is seeking treatment. As part of the admittance procedure, the healthcare facility may gather demographic attributes associated with the person and may forward those to the computing device along with a query requesting the identification of one or more patient records associated with the person who is seeking admittance.

The computing device 12 may also include means, such as the processing circuitry 20, the processor 22 or the like, for determining a digest based upon the demographic attributes associated with the person. The computing device, such as the processing circuitry, may be configured to determine the digest in various manners. In one embodiment, the computing device, such as the processing circuitry, is configured to determine the digest based upon the demographic attributes associated with the person in the same manner that the computing device, such as the processing circuitry, has determined the digest(s) of the patient records that have been received, such as described above in conjunction with blocks 32 and 34 of FIG. 3. As such, the computing device, such as the processing circuitry, may be configured to determine a fuzzy representation of one or more of the plurality of the demographic attributes associated with the person, such as the same demographic attributes for which fuzzy representations were determined in conjunction with the determination of the digest(s) of the patient records that have been received. See block 42 of FIG. 4. Alternatively, the computing device, such as the processing circuitry, may be configured to determine a digest based upon the demographic attributes associated with the person by combining representations of the demographic attributes without having determining and utilizing a fuzzy representation of the demographic attributes. In addition, the computing device, such as the processing circuitry, may be configured to combine representations of one of more of demographic attributes associated with the person including the fuzzy representation of one or more of the plurality of demographic attributes associated with the person. See block 44. In an embodiment in which the computing device, such as the processing circuitry, is configured to create more than one digest of the patient records received from the healthcare facilities using different combinations of representations of demographic attributes, as described above, the computing device, such as the processing circuitry, may also be configured to create corresponding digests for the patient record associated with the person. Similarly, in an embodiment in which the computing device, such as the processing circuitry, is configured to hash each digest of the patient records received from the healthcare facilities as described above in conjunction with block 36 of FIG. 3, the computing device, such as the processing circuitry, may also be configured to hash the digest of the patient record of the person in question. See block 46 of FIG. 4.

In respect to the query, the computing device 12 also include means such as the processing circuitry 20, the processor 22 or the like, for identifying one or more patient records that are associated with respective patients who are candidates to match the person. See block 48 of FIG. 4. In this regard, the computing device, such as the processing circuitry, may be configured to identify the potentially matching patient records based upon a comparison of the representations of the digests of the patient records and a representation of the digest(s) of the person. In this regard, the representations of the digests of the patient records and the representation of the digest of the person may simply be the digests of the patient records and the digest of the person in an embodiment in which the digests are not hashed, or, alternatively, the hashed representations of the digests of the patient records and the hashed representation of the digest of the person in an embodiment in which the digests are hashed.

The patient records that have digests that equal the digest of the person may be identified by the computing device 12, such as the processing circuitry 20, as being associated with patients who are candidates to match the person. As a result of the approximation or estimation of the demographic attributes attributable to the fuzzy representation of one or more of the plurality of demographic attributes associated with the patient, the patient records that are identified are associated with respective patients who are merely candidates to match the person, as opposed to being associated with respective patients who necessarily match the person. However, as a result of the approximation or estimation of the demographic attributes provided by the fuzzy representation of one or more of the plurality of demographic attributes associated a patient, the method, computing device and computer program product of an example embodiment may quickly and efficiently analyze many patient records, such as thousands, tens of thousands, hundreds of thousands or more patient records, and may identify a smaller subset of patient records that are associated with respective patients who are candidates to match the person.

In order to more conclusively identify the patient records that are associated with respective patients who match the person, the method, computing device and computer program product of an example embodiment may also be configured to perform a second phase of analysis upon the subset of patient records that have been identified as described above to be potential matches. While this second phase of analysis may be more time and processing intensive when considered on a per patient record basis, the substantial reduction in the number of patient records to be considered as a result of the identification of only a subset of the patient records as matching candidates still permits the method, computing device and computer program product of this embodiment to identify patient records that are associated with respective patients who are even stronger candidates to match the person in an efficient and timely manner, such as while the person awaits admittance to the healthcare facility.

In this embodiment, the computing device 12 may include means, such as the processing circuitry 20, the processor 22 or the like, for determining a confidence score for each patient record that was identified as a potential match by comparing the plurality of demographic attributes associated with respective patients to corresponding demographic attributes of the person. See block 40 of FIG. 4. The computing device of this embodiment may also include means, such as the processing circuitry or the like, for identifying one or more patient records that are associated with respective patients who match the person based upon the confidence scores, such as by identifying those patient records having a confidence score that satisfies a predefined threshold. See block 52 of FIG. 4. Based upon the patient records that are identified, the computing device, such as the processing circuitry, the communications interface 26 or the like, may then be configured in one embodiment to cause the patient records that are associated with respective patients who more strongly match the person to be provided to the healthcare facility at which the person is being admitted. As such, healthcare practitioners may review the patient records that are associated with respective patients who more strongly match the person in order to obtain a more comprehensive picture of the healthcare that was previously provided to the person so as to facility the current treatment of the person.

As described above, FIGS. 3 and 4 illustrate flowcharts of a system, method, and computer program product according to example embodiments of the invention. It will be understood that each block of the flowcharts, and combinations of blocks in the flowcharts, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices 24 of a computing device 12 and executed by processing circuitry 20 in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowcharts support combinations of means for performing the specified functions and combinations of steps for performing the specified functions. It will also be understood that one or more blocks of the flowcharts, and combinations of blocks in the flowcharts, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processing circuitry 20 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. A method implemented by a health information infrastructure, the method comprising:
    receiving, via a communication interface, a plurality of records, each record having a plurality of demographic attributes associated with an individual, wherein receiving the plurality of records comprises receiving only a portion of a plurality of patient records created by one or more healthcare facilities by receiving, from the one or more healthcare facilities for each of the plurality of patient records created by the one or more healthcare facilities, information defining the demographic attributes associated with the individual, but not receiving information associated with encounters of the individual with a healthcare facility and not receiving documents included in the patient record;
    for each record, determining, with processing circuitry, a digest by determining a fuzzy representation of one or more of the plurality of demographic attributes for the respective individual and combining by concatenating into a single string representations of one or more of the plurality of demographic attributes associated with the respective individual including the fuzzy representation of one or more of the plurality of demographic attributes associated with the respective individual;
    receiving a query relating to a record for a person and demographic attributes associated with the person;
    determining a digest based upon the demographic attributes associated with the person who is a subject of the query, wherein determining the digest comprises determining a fuzzy representation of one or more demographic attributes of the person who is the subject of the query and combining by concatenating into a single string representations of one or more of the demographic attributes of the person who is the subject of the query including the fuzzy representation of one or more demographic attributes of the person who is the subject of the query;
    in response to the query, identifying one or more records that are associated with respective individuals who are candidates to match the person based upon a comparison of representations of the digests of the records and a representation of the digest of the person;
    for each record that was identified and, as a result, for only a subset of the plurality of records, determining a confidence score by comparing the plurality of demographic attributes associated with the respective individuals to corresponding demographic attributes of the person;
    identifying one or more records that are associated with respective individuals who match the person based upon the confidence scores; and
    causing at least some of the one or more records that were identified based upon the confidence scores to be associated with respective individuals who are candidates to match the person to be provided via the communication interface.

2. A method according to claim 1 wherein determining a fuzzy representation comprises determining a fuzzy representation of a name by determining a phonetic representation of at least a subset of the name.

3. A method according to claim 1 wherein determining a fuzzy representation comprises determining a fuzzy representation of a date by determining a representation of the date with less specificity than a respective day.

4. A method according to claim 3 wherein determining a representation of the date comprises determining a representation of the date based upon a week, a month, a year or a decade of the respective day.

5. A method according to claim 1 wherein determining a digest comprises determining, for at least some records, a plurality of different digests.

6. A method according to claim 4 wherein the plurality of different digests are based upon a typographical error in a demographic attribute, transposition of first and last names of the respective individual or transposition of a day and month of a date.

7. A method according to claim 1 further comprising hashing the digests of the records and the digest of the person such that the comparison is based upon hashed representations of the digests of the records and a hashed representation of the digest of the person.

8. A method according to claim 1 further comprising communicating with the one or more healthcare facilities via an application programming interface (API) or via a portal application.

9. A computing device of a health information infrastructure, the computing device comprising a processing circuitry configured to:
    receive a plurality of records, each record having a plurality of demographic attributes associated with an individual, wherein the plurality of records are received by receiving only a portion of a plurality of patient records created by one or more healthcare facilities by receiving, from the one or more healthcare facilities for each of the plurality of patient records created by the one or more healthcare facilities, information defining the demographic attributes associated with the individual, but not receiving information associated with encounters of the individual with a healthcare facility and not receiving documents included in the patient record;
    for each record, determine a digest by determining a fuzzy representation of one or more of the plurality of demographic attributes for the respective individual and combining by concatenating into a single string representations of one or more of the plurality of demographic attributes associated with the respective individual including the fuzzy representation of one or more of the plurality of demographic attributes associated with the respective individual;

receive a query relating to a record for a person and demographic attributes associated with the person;

determine a digest based upon the demographic attributes associated with the person who is a subject of the query, wherein the digest is determined by determining a fuzzy representation of one or more demographic attributes of the person who is the subject of the query and combining by concatenating into a single string representations of one or more of the demographic attributes of the person who is the subject of the query including the fuzzy representation of one or more demographic attributes of the person who is the subject of the query;

in response to the query, identify one or more records that are associated with respective individuals who are candidates to match the person based upon a comparison of representations of the digests of the records and a representation of the digest of the person;

for each record that was identified and, as a result, for only a subset of the plurality of records, determine a confidence score by comparing the plurality of demographic attributes associated with the respective individuals to corresponding demographic attributes of the person;

identify one or more records that are associated with respective individuals who match the person based upon the confidence scores; and cause at least some of the one or more records that were identified based upon the confidence scores to be associated with respective individuals who are candidates to match the person to be provided via a communication interface.

10. A computing device according to claim 9 wherein the processing circuitry is configured to determine a fuzzy representation by determining a fuzzy representation of a name by determining a phonetic representation of at least a subset of the name.

11. A computing device according to claim 9 wherein the processing circuitry is configured to determine a fuzzy representation by determining a fuzzy representation of a date by determining a representation of the date with less specificity than a respective day.

12. A computing device according to claim 9 wherein the processing circuitry is configured to determine a digest by determining, for at least some records, a plurality of different digests.

13. A computing device according to claim 12 wherein the plurality of different digests are based upon a typographical error in a demographic attribute, transposition of first and last names of the respective individual or transposition of a day and month of a date.

14. A computing device according to claim 9 wherein the processing circuitry is further configured to hash the digests of the records and the digest of the person such that the comparison is based upon hashed representations of the digests of the records and a hashed representation of the digest of the person.

15. A computer program product of a health information infrastructure, the computer program product comprising a non-transitory computer readable storage medium having program code portions stored thereon, the program code portions configured, upon execution, to:

receive a plurality of records, each record having a plurality of demographic attributes associated with an individual, wherein the plurality of records are received by receiving only a portion of a plurality of patient records created by one or more healthcare facilities by receiving, from the one or more healthcare facilities for each of the plurality of patient records created by the one or more healthcare facilities, information defining the demographic attributes associated with the individual, but not receiving information associated with encounters of the individual with a healthcare facility and not receiving documents included in the patient record;

for each record, determine a digest by determining a fuzzy representation of one or more of the plurality of demographic attributes for the respective individual and combining by concatenating into a single string representations of one or more of the plurality of demographic attributes associated with the respective individual including the fuzzy representation of one or more of the plurality of demographic attributes associated with the respective individual;

receive a query relating to a record for a person and demographic attributes associated with the person;

determine a digest based upon the demographic attributes associated with the person who is a subject of the query, wherein the digest is determined by determining a fuzzy representation of one or more demographic attributes of the person who is the subject of the query and combining by concatenating into a single string representations of one or more of the demographic attributes of the person who is the subject of the query including the fuzzy representation of one or more demographic attributes of the person who is the subject of the query;

in response to the query, identify one or more records that are associated with respective individuals who are candidates to match the person based upon a comparison of representations of the digests of the records and a representation of the digest of the person;

for each record that was identified and, as a result, for only a subset of the plurality of records, determine a confidence score by comparing the plurality of demographic attributes associated with the respective individuals to corresponding demographic attributes of the person;

identify one or more records that are associated with respective individuals who match the person based upon the confidence scores; and cause at least some of the one or more records that were identified based upon the confidence scores to be associated with respective individuals who are candidates to match the person to be provided via a communication interface.

16. A computer program product according to claim 15 wherein the program code portions configured to determine a fuzzy representation comprise program code portions configured to:

determine a fuzzy representation of a name by determining a phonetic representation of at least a subset of the name; and determine a fuzzy representation of a date by determining a representation of the date with less specificity than a respective day.

17. A computer program product according to claim 15 wherein the program code portions configured to determine a digest comprise program code portions configured to determine, for at least some records, a plurality of different digests.

18. A computer program product according to claim 15 wherein the program code portions are further configured to hash the digests of the records and the digest of the person such that the comparison is based upon hashed representations of the digests of the records and a hashed representation of the digest of the person.

\* \* \* \* \*